(12) United States Patent
Stearns et al.

(10) Patent No.: US 9,022,987 B2
(45) Date of Patent: May 5, 2015

(54) DELIVERY SYSTEM FOR INJECTION THROUGH ZONE OF BODY

(75) Inventors: Stanley D. Stearns, Houston, TX (US);
H. Max Loy, Jr., Houston, TX (US);
Donald G. Davis, Baton Rouge, LA (US)

(73) Assignee: Gabriel Institute, Inc., Houston, TX (US)

( * ) Notice: Subject to any disclaimer, the term of this patent is extended or adjusted under 35 U.S.C. 154(b) by 688 days.

(21) Appl. No.: 13/298,742

(22) Filed: Nov. 17, 2011

(65) Prior Publication Data

US 2012/0065618 A1    Mar. 15, 2012

Related U.S. Application Data

(63) Continuation-in-part of application No. 12/276,637, filed on Nov. 24, 2008, now Pat. No. 8,529,516.

(60) Provisional application No. 61/078,674, filed on Jul. 7, 2008.

(51) Int. Cl.
*A61M 5/00* (2006.01)
*A61M 5/178* (2006.01)
*A61M 5/172* (2006.01)
*A61M 5/32* (2006.01)
*A61M 5/46* (2006.01)
*A61M 5/48* (2006.01)
(Continued)

(52) U.S. Cl.
CPC ......... *A61M 5/1785* (2013.01); *A61M 5/16886* (2013.01); *A61M 5/172* (2013.01); *A61M 5/32* (2013.01); *A61M 5/46* (2013.01); *A61M 5/484* (2013.01); *A61M 2202/049* (2013.01); *A61M 5/2053* (2013.01); *A61M 2205/3334* (2013.01); *A61M 2206/20* (2013.01)

(58) Field of Classification Search
CPC .................. A61M 5/19; A61M 2005/1787
USPC .................. 604/191, 187, 506, 194–195
See application file for complete search history.

(56) References Cited

U.S. PATENT DOCUMENTS

| 984,037 A | 2/1911 | Sheets |
| 4,392,859 A | 7/1983 | Dent |

(Continued)

OTHER PUBLICATIONS

Linda Sholl, International Preliminary Report on Patentability—PCT/US12/60818, Oct. 16, 2013, 6 pages, United States Patent and Trademark Office, Alexandria, Virginia USA.

(Continued)

*Primary Examiner* — Edelmira Bosques
(74) *Attorney, Agent, or Firm* — Crain, Caton & James, P.C.; James E. Hudson, III

(57) ABSTRACT

A dispensing device which disperses medicate through a needle across a zone within a body with zero pressure differential. The device includes a needle which is, during use, becomes encapsulated within a tubular needle-receiving member, a therapeutic agent reservoir in fluid communication with the needle, positioned within said housing, and in communication with the needle, a second reservoir, a reservoir-connecting conduit in communication with the therapeutic agent reservoir, a fluid drive in communication with the fluid in the second reservoir and in communication with said reservoir-connecting conduit, and a linear drive attached to said needle or to said needle-receiving member.

3 Claims, 4 Drawing Sheets

(51) Int. Cl.
*A61M 5/20* (2006.01)
*A61M 5/168* (2006.01)

(56) References Cited

U.S. PATENT DOCUMENTS

| | | | |
|---|---|---|---|
| 5,125,414 | A | 6/1992 | Dysarz |
| 5,891,105 | A | 4/1999 | Mahurkar |
| 6,056,716 | A | 5/2000 | D'Antonio et al. |
| 6,645,181 | B1 * | 11/2003 | Lavi et al. .............. 604/191 |
| 8,529,516 | B2 | 9/2013 | Stearns |
| 2002/0068907 | A1 * | 6/2002 | Dysarz ................ 604/191 |
| 2004/0050864 | A1 | 3/2004 | Stradella |
| 2010/0004604 | A1 | 1/2010 | Stearns |
| 2010/0049140 | A1 | 2/2010 | Marsh et al. |
| 2010/0185152 | A1 | 7/2010 | Larsen et al. |
| 2011/0238009 | A1 | 9/2011 | Meron et al. |

OTHER PUBLICATIONS

Blaine R. Copenheaver, Notification of Transmittal of the International Search Report and the Written Opinion of the International Searching Authority, or the Declaration; International Application No. PCT/US2012/060818; Jan. 2, 2013, 1 page, International Searching Authority, Alexandria, Virginia, US.

Blaine R. Copenheaver, International Search Report, International Application No. PCT/US2012/000818; Jan. 2, 2013, 2 pages, International Searching Authority, Alexandria, Virginia, US.

Blaine R. Copenheaver, Written Opinion of the International Searching Authority, International Application No. PCT/US2012/060818; Jan. 2, 2013, 4 pages, International Searching Authority, Alexandria, Virginia, US.

Linda Sholl, Notification of transmittal of International Preliminary Report on Patentability—PCT/US09/49669, Jul. 27, 2010, 1 page, United States Patent and Trademark Office as Examining Authority, Alexandria, Virginia, USA.

Linda Sholl, International Preliminary Report on Patentability—PCT/US09/49669, Jul. 27, 2010, 6 pages, United States Patent and Trademark Office as Examining Authority, Alexandria, Virginia, USA.

Webster's II New College Dictionary, pp. 19, 72, 1995, Houghton Mifflin Company, Boston, Massachusetts, USA.

* cited by examiner

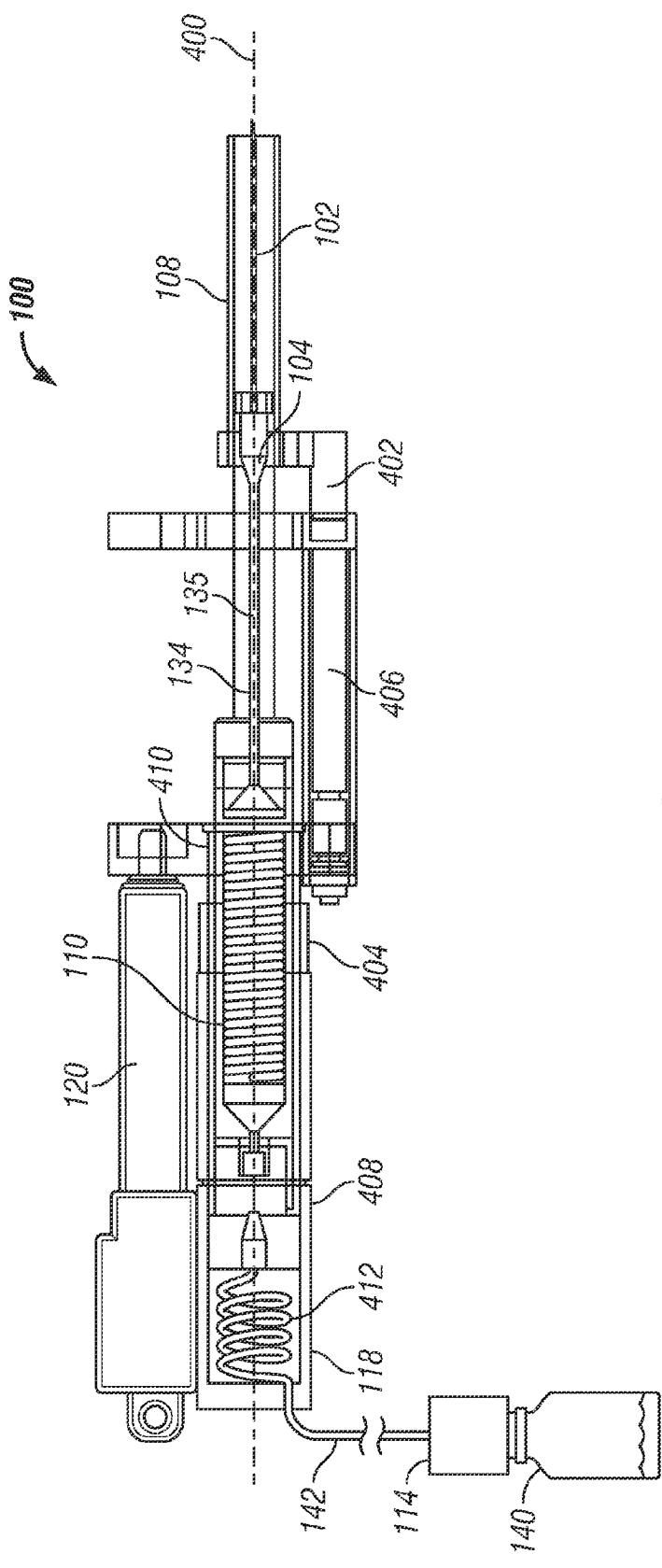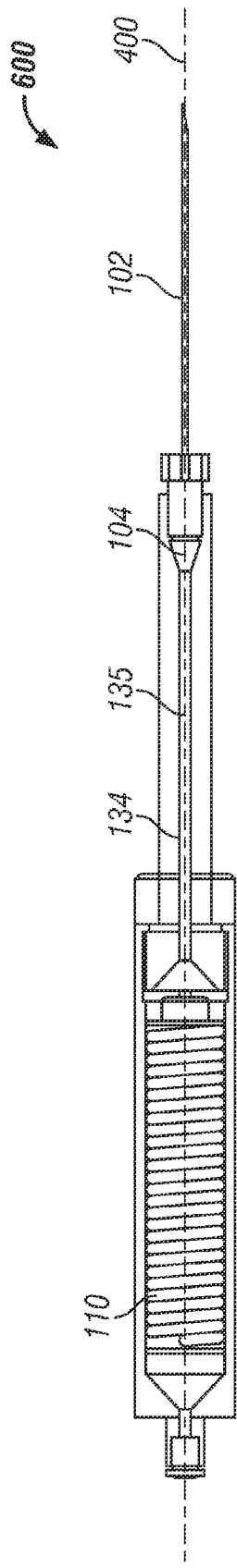

DELIVERY SYSTEM FOR INJECTION THROUGH ZONE OF BODY

CROSS REFERENCE TO RELATED APPLICATIONS

This application claims the benefit of U.S. Provisional Patent Application No. 61/078,674 entitled, "Syringe for injection through zone of body" filed on Jul. 7, 2008 in the United States Patent and Trademark Office and is a continuation-in-part of U.S. patent application Ser. No. 12/276,637, Syringe for injection through zone of body, filed Nov. 24, 2008.

STATEMENT REGARDING FEDERALLY SPONSORED RESEARCH OR DEVELOPMENT

Not Applicable.

BACKGROUND OF THE INVENTION

1. Field of the Invention

The present invention relates to an apparatus for delivery of medical treatment through a zone of a body. More particularly, the invention relates to automated devices and systems for the delivery and injection of therapeutic agents, solutions or injectates throughout a portion of bodily tissue. Additionally, the invention relates to methods of delivering and injecting a solution across a target site within the body for the treatment of that target site.

2. Description of the Related Art

Hypodermic syringes are widely used in the medical field for administering medicaments. Generally, hypodermic syringes include a needle having a sharpened distal point for penetrating vial stoppers or patient's body. The needle is attached either fixedly or removably to a syringe barrel. In operation, these syringes provide the means to deliver medicaments to a single specific location in the body. In operation, the plunger is depressed into the barrel and the medicament thus discharged. This system, largely unchanged since the invention of the syringe, contemplates delivery of the therapeutic agent at a single location wherein the effect of the therapeutic agent is transmitted through adjacent cells. Problematically, when the therapeutic agent is intended to act against a collection of cells, its effectiveness is reduced and/or delayed by such transmission, even though the overall distance from one side of the collection of cells to the other may be quite small. Practitioners have attempted to overcome this limitation and provide the benefit of a dispersed delivery by simultaneously depressing the syringe plunger with the thumb while also withdrawing the syringe. However, this technique is difficult to learn and is ineffective to properly deliver the therapeutic agent to the desired location in the desired quantities, particularly when the desired location has defined boundaries, such as a tumor.

Additionally, delivery systems have been constructed to provide delivery of a therapeutic agent with an automated system. However, these systems either suffer the same shortcomings as conventional syringes or suffer from the necessity to provide the therapeutic agent into a dynamic system, such as blood flow, which results in the undesirable distribution of therapeutic agents throughout the body instead of localized distribution.

Further, when the therapeutic agent poses a danger to care providers, such as in the case radioactive agents, it is desirable to minimize the exposure to the care provider, particularly by limiting the time of exposure to the care provider, by providing a delivery system which inhibits or prevents exposure, and by providing a delivery system which limits the extent of therapeutic agent used.

There is therefore a need for a delivery system that disburses a therapeutic agent along a path of a collection of cells in a body by automated means.

SUMMARY OF THE INVENTION

It is therefore, a principle object of the present invention to provide a delivery system which disburses a therapeutic agent along the path of a collection of cells in a body based on limited action by the operator.

In particular, a principal object of the present invention is to provide a system utilizing a delivery device which retracts the needle as fluid is dispensed into the body, wherein the fluid is stored in a reservoir and delivered via a pump or separate syringe coordinated with the movement of the retracting needle in a manner wherein the necessary therapeutic agent is delivered and wherein none remains in the system at the end of use. The needle moves in such a fashion as to introduce the fluid with a zero pressure differential while the therapeutic agent is pushed forward, preferably with another fluid. Thus, in the case of introduction of a radioactive agent, the exposure to radiation by the care provider or technician is reduced. The unit may be hand-held or robotic. Thus, fluid is not "squirted" from the needle, but rather deposited along a path during retraction of the needle. As the needle may be introducing a radioactive therapeutic agent, the needle is ideally encapsulated by a shielding needle-receiving member.

The foregoing advantages are achieved through a device which includes a needle which is, during use, encapsulated within a tubular needle-receiving member, a therapeutic agent reservoir in fluid communication with the needle, positioned within said housing, and in communication with the needle, a second reservoir, a reservoir-connecting conduit in communication with the therapeutic agent reservoir, a fluid drive in communication with the fluid in the second reservoir and in communication with said reservoir-connecting conduit, and a linear drive attached to said needle or to said needle-receiving member. Preferably, the linear drive provides a linear displacement of either the needle or the needle-receiving member at a constant rate so the product of said linear displacement and internal cross-sectional area of said needle determines a volume of displacement and a flow rate and the fluid drive impel fluid from said second reservoir to said a reservoir-connecting conduit, which may be non-therapeutic at the flow rate during said linear displacement and which pushes the therapeutic agent fluid from the therapeutic agent reservoir and into the needle during its retraction from the body.

In operation, a needle having an internal cross-sectional area is driven into the body and then retracted at a fixed velocity by a linear drive into a housing including a needle receiving member so that the needle is encapsulated during retraction. The product of the velocity of retraction and the cross sectional area of the needle provide a flow rate. During retraction, fluid from a second reservoir is impelled by a pump through a reservoir-connecting conduit to a therapeutic agent reservoir, preferably a coil of tubing, containing said therapeutic agent at the determined flow rate. By virtue of the small cross sectional area and diameter of the tubing comprising the therapeutic agent reservoir, the therapeutic agent is displaced without mixing with the fluid and is ejected from the needle at predetermined flow rate, resulting in a zero pressure differential during injection, while the needle is being retracted.

The foregoing and other objectives, features and advantages of the invention will be more readily understood upon consideration of the following detailed description of the invention, taken in conjunction with the accompanying drawings.

BRIEF DESCRIPTION OF THE DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only a typical preferred embodiment of the invention and are therefore not to be considered limiting of its scope as the invention may admit to other equally effective embodiments.

FIG. 5 illustrates the first alternative embodiment of the invention in its final position.

FIG. 6 illustrates a cartridge assembly which may be employed in the alternative embodiment.

DETAILED DESCRIPTION OF THE PREFERRED EMBODIMENT

The present invention involves an improvement of delivery of an injection through a zone of a body. More particularly, the invention involves a syringe for the delivery and injection of therapeutic agents, solutions or injectates over a portion of bodily tissue rather than in a single location, which apparently functioning as a conventional syringe.

Ideally, the invention provides an injection system which distributes therapeutic agent along a line of injection during removal of the needle from the body with a zero pressure differential. The system includes a needle, a housing with a tubular needle-receiving member, a therapeutic agent reservoir, a second reservoir, a reservoir-connecting conduit, a fluid drive, and a linear drive.

Figure 1:
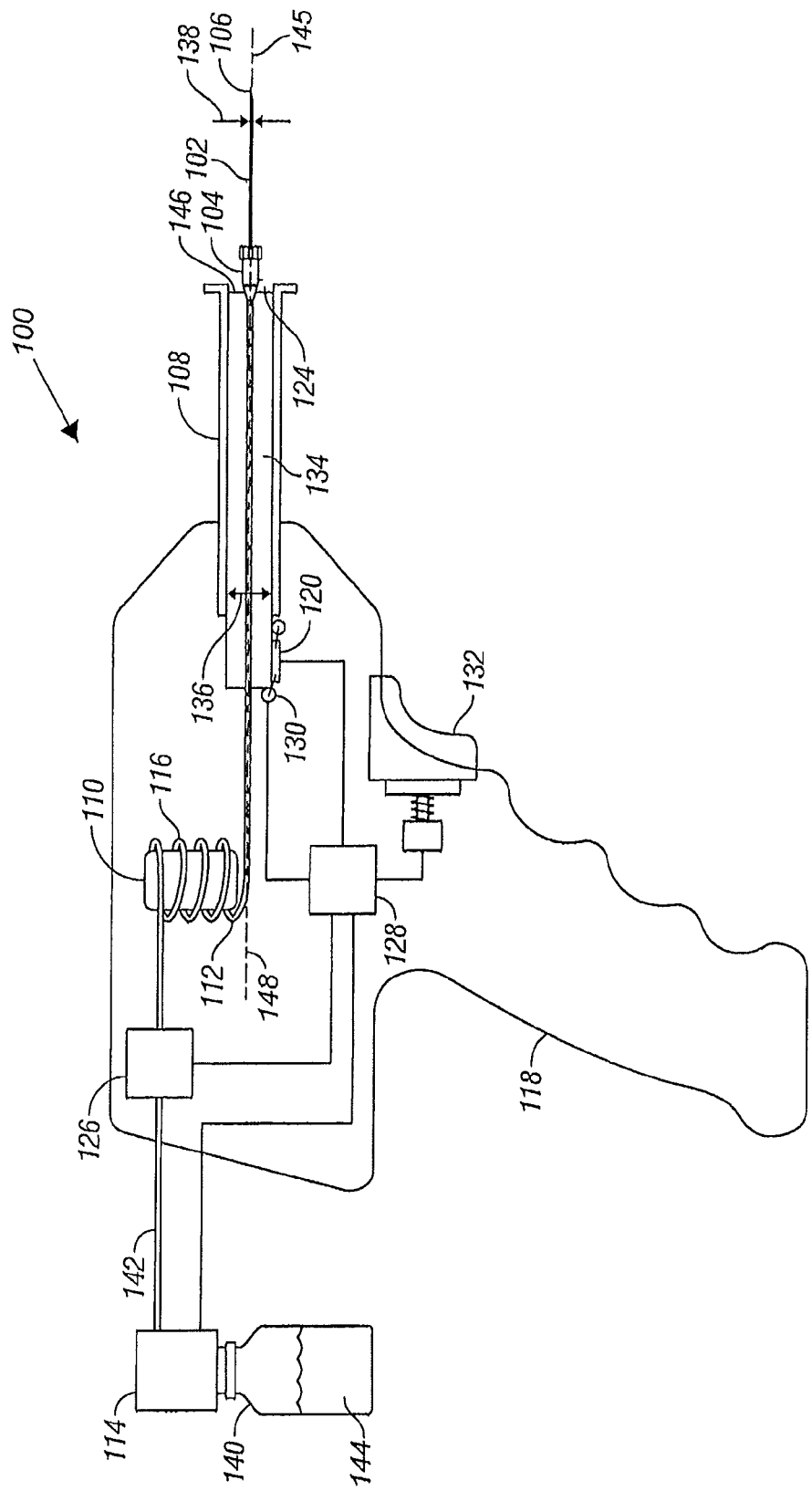
FIG. 1 illustrates an embodiment of the invention in its initial position.

Referring to FIG. 1, the distributed injection device 100 includes a needle 102, a housing 118 which includes a needle-receiving member 108, a therapeutic agent reservoir 110, a second reservoir 140, a reservoir-connecting conduit 142, a fluid drive 114, and a linear drive 120. Housing 118 may be constructed in any form capable of containing the necessary elements and providing ease of use, including in a pistol-grip style depicted in FIG. 1 or in the rod-grip style depicted in FIGS. 4 and 5.

Figure 2:
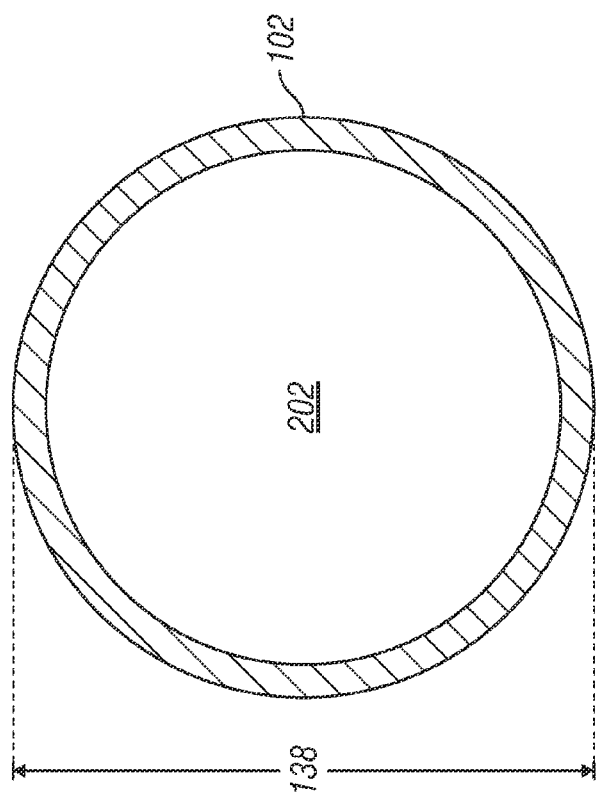
FIG. 2 illustrates the cross-sectional area of the needle of the present invention.

The needle 102 has an attachment end 104 and an injection end 106 and a needle outer diameter 138. This structure further defines the internal cross-sectional area 202 of the needle 102 (as depicted in FIG. 2) and defines the needle longitudinal axis 145 of the needle 102. The injection end 106 of the needle 102, as would be expected, may be sharpened to a prong to aid in penetration or may be flat if directed into a preexisting entry. Preferably, the needle 102 is affixed at its attachment end 104 to a slide member 134 at the slide member's first end 146 to reduce the length of needle needed for operation.

Constructed to ultimately surround the needle 102 after retraction and to provide shielding during retraction is a needle-receiving member 108. The needle-receiving member 108 is tubular and has an open first end 124 to communicate with the needle 102. As can be appreciated, to provide ease of retraction, the needle-receiving member 108 has a needle-receiving member inner diameter 136 greater than the needle outer diameter 138. Consistent with the retraction and shielding functions, the needle-receiving member 108 has a needle-receiving member longitudinal axis 148 generally parallel to the needle longitudinal axis and circumscribed within the needle-receiving member.

The therapeutic agent reservoir 110 is adapted to contain a therapeutic agent 116 for delivery to the needle. Thus, the therapeutic agent reservoir 110 is in fluid communication with the needle 102 via a tubing 198 to facilitate the flow of the therapeutic agent 116 from the therapeutic agent reservoir 110 to the needle 102 and thereafter for injection in the body. Preferably, the therapeutic agent reservoir 110 is positioned within the housing 118 which is constructed to provide a safe barrier to the contents of the therapeutic agent 116, particularly where the therapeutic agent 116 may be radioactive. Ideally, the therapeutic agent reservoir 110 is created by a length of narrow tubing, preferably of cross-sectional area equivalent to the cross sectional area of the needle 102. The surface tension associated with the interior walls of the therapeutic agent reservoir 110 and its small cross-sectional area is ideally selected to ensure the therapeutic agent 116 exhibits near-capillary action. Thus, the therapeutic agent 116 can flow through the therapeutic agent reservoir 110 but maintains itself as a cohesive flow without mixing with any upstream flow.

A second reservoir 140 is adapted to contain a fluid 144, which is preferably chemically distinct from the therapeutic agent 116, particularly not intended as a therapeutic agent, e.g. saline, and does not create the dangers associated with therapeutic agent 116.

A reservoir-connecting conduit 142, preferably having an interior diameter equivalent to that of the therapeutic agent reservoir 110, is provided on the upstream side of the therapeutic agent reservoir 110 and is in communication with the therapeutic agent reservoir 110.

Intermediate the second reservoir 140 and the reservoir-connecting conduit 142, or otherwise positions to drive fluid from the second reservoir 140 to the reservoir-connecting conduit 142, is a fluid drive 114, such as a pump, in communication with the fluid 144 in the second reservoir 140 and in communication with the reservoir-connecting conduit 142. When engaged, the fluid drive 114 draws or directs fluid 144 from the second reservoir 140 and through the reservoir-connecting conduit 142. Because of the small cross-sectional area of the therapeutic agent reservoir 110, the fluid 144 from the second reservoir pushes the therapeutic agent 116 through therapeutic agent reservoir 110 without mixing. Moreover, due to the small cross-sectional area and the surface tension within the reservoir-connecting conduit 142 and the therapeutic agent reservoir 110, a bubble of air, if desired as a separator, may be introduced intermediate the fluid 144 and the therapeutic agent 116.

Figure 3:
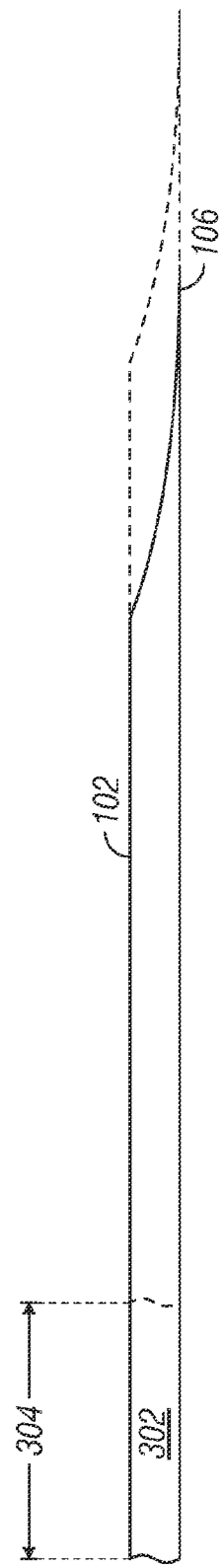
FIG. 3 illustrates the volume displacement of fluid during the displacement of the needle relative to the receiving member.
Figure 4:
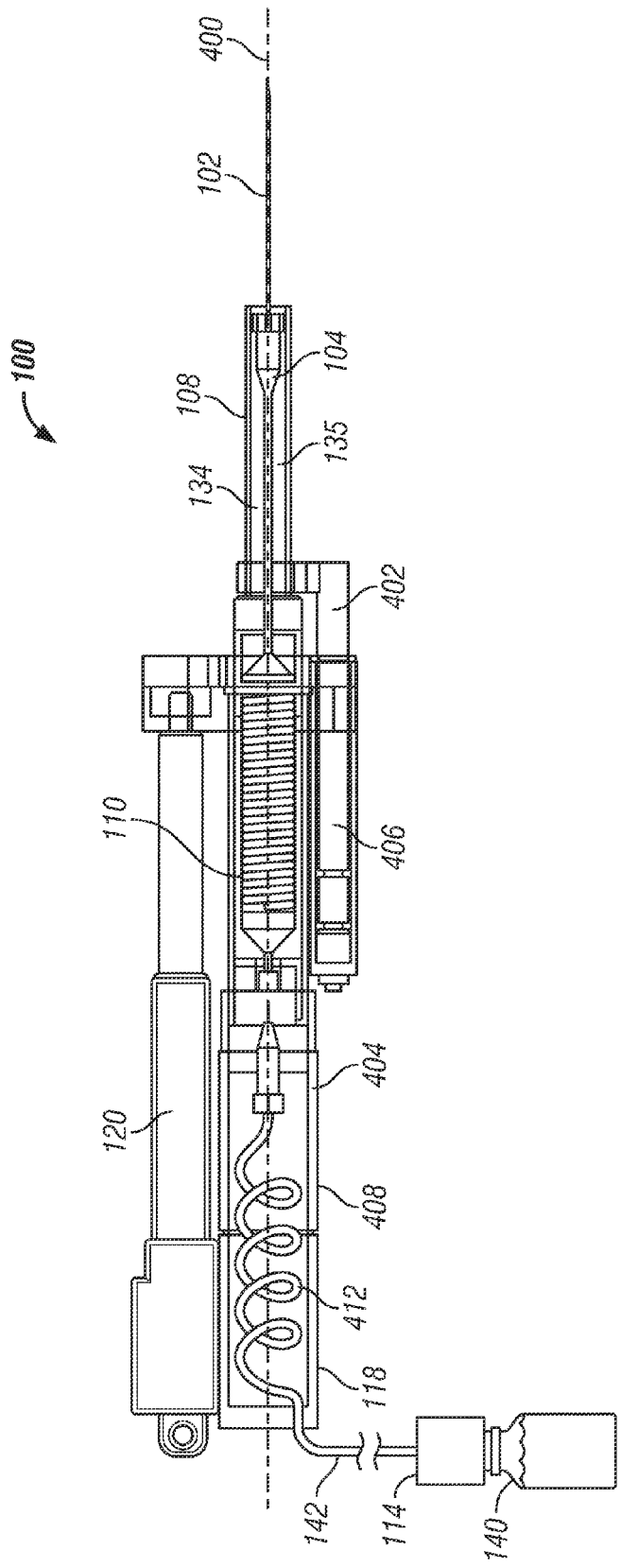
FIG. 4 illustrates an alternative embodiment of the invention in its initial position.

Finally, the device includes a linear drive 120 associated with the needle 102 or the needle-receiving member 108. During delivery of the therapeutic agent 116, pushed by the fluid 144 from the second reservoir 140 by fluid drive 114 through connecting conduit 142, the needle 102 is retracted from the body at a fixed rate. As depicted in FIG. 3, the product of the displacement 304 of the needle 102 from the linear drive 120 and the internal cross-sectional area of the needle 102 provides the volume of displacement 302, and, in connection with the displacement per unit time, provides a flow rate. As a result of the structure, needle-retraction rate and flow rate form the fluid drive 114, the flow rate through the needle 102 is equal to the volume created per unit time for injection with the withdrawal of the needle 102 from the body. Thus, the flow rate delivers the therapeutic agent 116 with zero pressure differential. This zero pressure differential cannot be achieved by human operation and ensures the therapeutic agent 116 is delivered exactly where desired and in the indented volume. Referring to FIG. 1, the linear drive 120 may be affixed to the needle 102, or may be affixed to a slide member 134 sized to slideably fit within the needle-receiving member 108, to provide a fitting for the needle 102 to ensure its rigid operation. The slide member 134 may include an internal passage 135 sized for the tubing 112 to pass through and connect directly to the needle 102 or may include an internal passage 135 having fittings at each end to connect to the needle 102 and the tubing 112 and thereby provide a conduit. The linear drive 120 may thereafter be fixed to housing 118 or the needle-receiving member 108 or other fixed components to ensure retraction of the needle 102 during operation, ultimately resulting in the repositioning of the needle 102 as depicted in FIGS. 4 and 5. Alternatively, the linear drive 120 may be affixed to the needle receiving member 108 to drive the needle-receiving member 108 towards the needle 102, resulting in encapsulating of the needle 102 while simultaneously repositioning the device 100 relative to the body, equivalent to the retraction of the needle 102, particularly helpful in providing immediate assessment of the extent of retraction of needle 102. The slide member 134 may also provide for a location for positioning of tubing 112 between the needle 102 and the reservoir 110.

Referring to FIGS. 4 and 5, the rod-style grip, the distributed injection device 100 provides the needle 102, the needle receiving member 108, the therapeutic agent reservoir 110, and the linear drive 120 associated with the housing 118, and the second reservoir 140, and fluid drive 114 external the housing 118 and connected via the reservoir-connecting conduit 142. FIG. 4 depicts the rod-style grip of the distributed injection device 100 prior to and at the time of injection, whereby the needle 102 is at its most extended position. The alternative embodiment depicted in FIGS. 4 and 5 provides for the linear drive 120 to contract, thus repositioning the needle 102 into the needle receiving member 108 best described as retraction of the needle 102. FIG. 5 depicts the rod-style grip version of the distributed injection device 100 at the end of use, when the linear drive 120 is fully engaged (retracted) and the needle 102 is fully encapsulated.

As with the first embodiment, the needle 102 is affixed at its attachment end 104 to a slide member 134 which is repositioned within the needle-receiving member 108. All components in the rod-style grip are aligned with the longitudinal axis 400 of the distributed injection device 100.

The therapeutic agent reservoir 110 may be created by a length of narrow tubing as provided above, coiled about a portion of the slide member 134.

As depicted in FIGS. 4 and 5, the needle 102 is positioned at one end of the injection device 100 and is connected, preferably by the detachable fitting known in the art, to a slide member 134 having an internal passage 135 therethrough and which is connected to the therapeutic agent reservoir 110, the substantial length of which is coiled about the upper portion of the slide member 134. The receiving member 108 may be associated with a guide arm 402 extending from the upper portion 404 of the housing 118 to maintain position and alignment during operation. The guide arm 402 may extend a length equal to the stroke of the linear drive 120 to provide the retraction of the needle 102 while maintaining position relative to the patient. To reduce binding, the guide arm 402 may telescope from a passage 406 and may, if desired, be loaded via a spring. The linear drive 120, which may be a piston-cylinder assembly, may be positioned opposite the slide member 134 from the guide arm 402 and may extend to drive the receiving member 108 forward and thus retract the needle 102. Thus, unlike the first embodiment where the linear drive 120 moves in the same direction as the needle 102, in the second embodiment the linear drive 120 moves relative to the needle 102 and therefore apparently in opposition.

Referring to FIGS. 4 and 5, and most particularly to FIG. 6, for ease of installation into the housing 118, the needle 102 and the therapeutic agent reservoir 110 may be incorporated into a single cartridge unit 600 for ease of installation and removal. Referring to FIGS. 4 and 5, the tubing 142 from the second reservoir 140 to the therapeutic agent reservoir 110 may include a coiled portion above the slide member 134, constructed to flex during operation of the linear drive 120 when the therapeutic agent reservoir 110, together with the slide member 134 travels downward.

The cartridge 600 is mounted in a telescoping tube receiver 408 which expands during initial operation of the linear drive 120 incident to retraction of the needle 102 from a body due to the advance of the needle-receiving member 108. The telescoping tube receiver 408 houses the end of a conduit 412 which is coiled to absorb the travel of the telescoping tube receiver 408. The telescoping tube receiver 408 is secured to the linear actuator via a mount block 410 which advances the telescoping tube receiver 408, causing it to telescopically extend. The coiled conduit 412 exits from the top of the telescoping tube receiver 408 and is connected to the conduit 142 from the second reservoir 140.

Beneficially, by locating within the housing 118 of the device 100 all those components which are in contact with the therapeutic agent 116 or irradiated by its energy, after use the therapeutic agent reservoir 110, the tubing 112, and the needle 102 may be removed for isolation and destruction and the housing 118, which may have provided shielding, placed in isolation or cleaned for subsequent use. Thus, a cartridge 600 By locating the non-therapeutic units (second reservoir 140, fluid drive 114 and reservoir-connecting conduit 142) external of the housing 118, which is not necessarily required, these units do not need to be discarded or placed in isolation and can therefore be immediately used thereafter. This may be particularly helpful if the volume of therapeutic reservoir 110 provides less volume of therapeutic agent 116 than needed during an operating session. Alternatively, all components can be located within the housing 118 to provide a self-contained device. However, all components will thereafter be subject to post-use restrictions and potential isolation, requiring disposal of the fluid 114 consistent with more stringent requirements.

To the extent the therapeutic fluid 116 contains radioisotopes, the housing 118 and the receiving member 108 may be constructed of or coated with a shielding material to protect the operator from radiation emitted from the needle 102 where the fluid 116 is radioactive. In the preferred embodiment, receiving member 108 is preferably constructed of tungsten. The reservoir 110 may also be constructed of or coated with a shielding material to protect the operator in such an instance. For example, if a radioisotope is selected who energy is unable to pass through plastic, then the components may include a plastic layer or may be composed of plastic.

In one embodiment, as illustrated in FIG. 1, a flow meter 126 may be positioned intermediate the second reservoir 110 and the needle 102 and may provide data to a computer 128 to compare with data from a linear positioning sensor 130 to ensure the flow rate from the reservoir 110 is equal to the flow rate associated with the retraction of the needle 102 through the body.

The housing 118 may include an operating switch 132 which permits the operator to simultaneously activate the linear drive 120 and the fluid drive 114 to ensure the deposition of fluid 116 at the injection end 106 of the needle 102 along the path of needle 102 during retraction.

After use, the needle 102, the reservoir 110 and any tubing 112 may be removed from the housing 118 for disposal in compliance with safety regulations and the balance of the components not contacting the fluid 116 used again.

The present invention provides significant advantages over the prior art. When high pH radioisotopes are used in treating illness, it is undesirable for the radioisotope to mix with the blood. Rather, it is desirable to deposit the radioisotope along a line in the tissue, particularly along the path of the needle 102 through the body tissue. It appears the high pH radioisotope typically reacts with the tissue, causing coagulation of the microcapillaries and precluding entry of the radioisotope into the bloodstream. Injection of the total volume of the liquid, however, does cause undesirable loss of the radioisotope into the bloodsteam. Ideally, a plurality of injection lines are utilized, as the range of the radioisotope is quite small, often in the range of six (6) millimeters (mm) on each side of the injection line. A plurality of injection lines, each corresponding to the needle path, therefore, blankets the tumor, with a substantial portion, potentially nearing ninety percent (90%) of the radioisotope remaining in the tumor and being effective there, with only a de minimus portion entering the remainder of the body, in quantities sufficiently low to pose a substantially lower risk of injury that current methods.

Various alternatives and/or modifications may be made to the disclosed embodiments without departing from the spirit or scope of the invention.

We claim:

1. A distributed injection device, comprising a needle, said needle having an attachment end and an injection end, said needle having a needle outer diameter, and said needle having an internal cross-sectional area, said needle having a needle longitudinal axis;

a housing including a needle-receiving member, said needle-receiving member being tubular, said needle-receiving member having an open first end, said needle-receiving member having a needle-receiving member inner diameter, said needle-receiving member inner diameter greater than said needle outer diameter, said needle-receiving member having a needle-receiving member longitudinal axis, said needle longitudinal axis and said needle-receiving member longitudinal axis generally parallel, said needle-receiving member circumscribing said needle longitudinal axis;

a therapeutic agent reservoir adapted to contain a therapeutic agent, said therapeutic agent reservoir in fluid communication with said needle via a tubing, said therapeutic agent reservoir positioned within said housing;

a second reservoir adapted to contain fluid;

a reservoir-connecting conduit, said reservoir-connecting conduit in communication with said therapeutic agent reservoir;

a fluid drive in communication with said fluid in said second reservoir, said fluid drive in communication with said reservoir-connecting conduit; and a linear drive associated with said needle or said needle-receiving member; said linear drive adapted to provide a linear displacement of said needle towards said housing, or to provide a linear displacement of said needle-receiving member away from said housing, the product of said linear displacement and internal cross-sectional area of said needle providing a volume of displacement, said volume of displacement per unit time providing a flow rate;

wherein said fluid drive adapted to impel fluid from said second reservoir to said reservoir-connecting conduit and to drive said therapeutic agent from said therapeutic agent reservoir at said flow rate during said linear displacement of said needle towards said housing, and wherein said fluid communication from said therapeutic agent reservoir to said needle is maintained by said tubing during operation of said linear drive to provide a linear displacement of said needle towards said housing, or to provide a linear displacement of said needle-receiving member away from said housing.

2. The distributed injection device of claim 1 further comprising a slide member, said needle fixed in position at a first end of said slide member, said slide member slidably positioned within said receiving member; and said linear drive connected to said slide member.

3. A method for a distributed injection into a body from a reservoir of therapeutic agent, comprising:

driving a needle into said body, said needle having an internal cross-sectional area;

retracting said needle from said body at a fixed velocity by a linear drive into a housing including a needle receiving member, said needle being encapsulated by said needle-receiving member during retraction, the product of said velocity and said cross-sectional area providing a flow rate;

impelling fluid from a second reservoir through a reservoir-connecting conduit to a therapeutic agent reservoir containing said therapeutic agent at said flow rate;

commencing impelling said therapeutic agent from said therapeutic agent reservoir to said needle by displacement by said fluid at said flow rate upon beginning retracting said needle from said body at a fixed velocity; and delivering said therapeutic agent from said needle into said body at zero pressure differential after commencing impelling said therapeutic agent from said therapeutic agent reservoir.

* * * * *